United States Patent
Olson (10) Patent No.: US 8,469,979 B2
(45) Date of Patent: *Jun. 25, 2013

(54) HIGH CAPACITY DEBULKING CATHETER WITH DISTAL DRIVEN CUTTING WHEEL

(75) Inventor: William John Olson, Menlo Park, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/239,820

(22) Filed: Sep. 22, 2011

(65) Prior Publication Data

US 2012/0016395 A1    Jan. 19, 2012

Related U.S. Application Data (63) Continuation of application No. 11/934,680, filed on Nov. 2, 2007, now Pat. No. 8,052,704.

(51) Int. Cl.
*A61B 17/22* (2006.01)

(52) U.S. Cl.
USPC ............... 606/159; 606/170; 600/439

(58) Field of Classification Search
USPC ......... 606/155, 159, 170, 167, 171, 180, 606/198, 186; 600/459, 564, 164.01, 508
See application file for complete search history.

(56) References Cited

U.S. PATENT DOCUMENTS

| | | |
|---|---|---|
| 1,481,078 A | 1/1924 | Albertson |
| 2,178,790 A | 11/1939 | Henry |
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |

(Continued)

FOREIGN PATENT DOCUMENTS

| | | |
|---|---|---|
| CA | 2000621 | 4/1990 |
| DE | 3732236 C1 | 12/1988 |

(Continued)

OTHER PUBLICATIONS

Jul. 19, 2011 Communication in European Application No. 04760155.4 (5 pages).

(Continued)

*Primary Examiner* — Tuan V Nguyen
(74) *Attorney, Agent, or Firm* — Alana T. Bergman, Esq.

(57) ABSTRACT

An atherectomy catheter with a rotary cutting element is provided. The catheter collects plaque shavings in a hollow collection chamber. The catheter includes a drive shaft connected between a source of rotational power and the distal side of the cutting element, no part of the drive shaft being contained within the collection chamber.

15 Claims, 5 Drawing Sheets

U.S. PATENT DOCUMENTS

| | | |
|---|---|---|
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,622 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMichael et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |

| Patent No. | Date | Inventor(s) |
|---|---|---|
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |

| | | | | | | |
|---|---|---|---|---|---|---|
| 5,820,592 | A | 10/1998 | Hammerslag | 6,159,195 A | 12/2000 | Ha et al. |
| 5,823,971 | A | 10/1998 | Robinson et al. | 6,159,225 A | 12/2000 | Makower |
| 5,824,039 | A | 10/1998 | Piplani et al. | 6,165,127 A | 12/2000 | Crowley |
| 5,824,055 | A | 10/1998 | Spiridigliozzi et al. | 6,179,859 B1 | 1/2001 | Bates et al. |
| 5,827,201 | A | 10/1998 | Samson et al. | 6,183,432 B1 | 2/2001 | Milo |
| 5,827,229 | A | 10/1998 | Auth et al. | 6,187,025 B1 | 2/2001 | Machek |
| 5,827,304 | A | 10/1998 | Hart | 6,190,353 B1 | 2/2001 | Makower et al. |
| 5,827,322 | A | 10/1998 | Williams | 6,191,862 B1 | 2/2001 | Swanson et al. |
| 5,830,224 | A | 11/1998 | Cohn et al. | 6,193,676 B1 | 2/2001 | Winston et al. |
| 5,836,957 | A | 11/1998 | Schulz et al. | 6,196,963 B1 | 3/2001 | Williams |
| 5,843,022 | A | 12/1998 | Willard et al. | 6,206,898 B1 | 3/2001 | Honeycutt et al. |
| 5,843,103 | A | 12/1998 | Wulfman | 6,217,527 B1 | 4/2001 | Selmon et al. |
| 5,843,161 | A | 12/1998 | Solovay | 6,217,549 B1 | 4/2001 | Selmon et al. |
| 5,855,563 | A | 1/1999 | Kaplan et al. | 6,217,595 B1 | 4/2001 | Shturman et al. |
| 5,865,748 | A | 2/1999 | Co et al. | 6,221,049 B1 | 4/2001 | Selmon et al. |
| 5,868,685 | A | 2/1999 | Powell et al. | 6,221,332 B1 | 4/2001 | Thumm et al. |
| 5,868,767 | A | 2/1999 | Farley et al. | 6,228,049 B1 | 5/2001 | Schroeder et al. |
| 5,871,536 | A | 2/1999 | Lazarus | 6,228,076 B1 | 5/2001 | Winston et al. |
| 5,873,882 | A | 2/1999 | Straub et al. | 6,231,546 B1 | 5/2001 | Milo et al. |
| 5,876,414 | A | 3/1999 | Straub | 6,231,549 B1 | 5/2001 | Noecker et al. |
| 5,879,397 | A | 3/1999 | Kalberer et al. | 6,235,000 B1 | 5/2001 | Milo et al. |
| 5,883,458 | A | 3/1999 | Sumita et al. | 6,238,405 B1 | 5/2001 | Findlay, III et al. |
| 5,888,201 | A | 3/1999 | Stinson et al. | 6,241,667 B1 | 6/2001 | Vetter et al. |
| 5,895,399 | A | 4/1999 | Barbut et al. | 6,241,744 B1 | 6/2001 | Imran et al. |
| 5,895,402 | A | 4/1999 | Hundertmark et al. | 6,245,012 B1 | 6/2001 | Kleshinski |
| 5,902,245 | A | 5/1999 | Yock | 6,258,052 B1 | 7/2001 | Milo |
| 5,910,150 | A | 6/1999 | Saadat | 6,263,236 B1 | 7/2001 | Kasinkas et al. |
| 5,911,734 | A | 6/1999 | Tsugita et al. | 6,264,611 B1 | 7/2001 | Ishikawa et al. |
| 5,916,210 | A | 6/1999 | Winston | 6,266,550 B1 | 7/2001 | Selmon et al. |
| 5,922,003 | A | 7/1999 | Anctil et al. | 6,277,138 B1 | 8/2001 | Levinson et al. |
| 5,935,108 | A | 8/1999 | Katoh et al. | 6,283,951 B1 | 9/2001 | Flaherty et al. |
| 5,938,645 | A | 8/1999 | Gordon | 6,283,983 B1 | 9/2001 | Makower et al. |
| 5,938,671 | A | 8/1999 | Katoh et al. | 6,299,622 B1 | 10/2001 | Snow et al. |
| 5,938,672 | A | 8/1999 | Nash | 6,299,623 B1 | 10/2001 | Wulfman |
| 5,941,869 | A | 8/1999 | Patterson et al. | 6,302,875 B1 | 10/2001 | Makower et al. |
| 5,947,985 | A | 9/1999 | Imran | 6,305,834 B1 | 10/2001 | Schubert et al. |
| 5,948,184 | A | 9/1999 | Frantzen et al. | 6,312,444 B1 | 11/2001 | Barbut |
| 5,951,480 | A | 9/1999 | White et al. | 6,319,242 B1 | 11/2001 | Patterson et al. |
| 5,951,482 | A | 9/1999 | Winston et al. | 6,319,275 B1 | 11/2001 | Lashinski et al. |
| 5,954,745 | A | 9/1999 | Gertler et al. | 6,330,884 B1 | 12/2001 | Kim |
| 5,968,064 | A | 10/1999 | Selmon et al. | 6,355,005 B1 | 3/2002 | Powell et al. |
| 5,972,019 | A | 10/1999 | Engelson et al. | 6,361,545 B1 | 3/2002 | Macoviak et al. |
| 5,985,397 | A | 11/1999 | Witt et al. | 6,375,615 B1 | 4/2002 | Flaherty et al. |
| 5,989,281 | A | 11/1999 | Barbut et al. | 6,383,195 B1 | 5/2002 | Richard |
| 5,997,557 | A | 12/1999 | Barbut et al. | 6,383,205 B1 | 5/2002 | Samson et al. |
| 6,001,112 | A | 12/1999 | Taylor | 6,394,976 B1 | 5/2002 | Winston et al. |
| 6,010,449 | A | 1/2000 | Selmon et al. | 6,398,798 B2 | 6/2002 | Selmon et al. |
| 6,010,522 | A | 1/2000 | Barbut et al. | 6,422,736 B1 | 7/2002 | Antonaides et al. |
| 6,013,072 | A | 1/2000 | Winston et al. | 6,423,081 B1 | 7/2002 | Lee et al. |
| 6,019,778 | A | 2/2000 | Wislon et al. | 6,425,870 B1 | 7/2002 | Flesch |
| 6,022,362 | A | 2/2000 | Lee et al. | 6,428,551 B1 | 8/2002 | Hall et al. |
| 6,027,450 | A | 2/2000 | Brown et al. | 6,428,552 B1 | 8/2002 | Sparks |
| 6,027,460 | A | 2/2000 | Shturman | 6,443,966 B1 | 9/2002 | Shiu |
| 6,027,514 | A | 2/2000 | Stine et al. | 6,445,939 B1 | 9/2002 | Swanson et al. |
| 6,032,673 | A | 3/2000 | Savage et al. | 6,447,525 B2 | 9/2002 | Follmer et al. |
| 6,036,646 | A | 3/2000 | Barthe et al. | 6,451,036 B1 | 9/2002 | Heitzmann et al. |
| 6,036,656 | A | 3/2000 | Slater | 6,454,779 B1 | 9/2002 | Taylor |
| 6,036,707 | A | 3/2000 | Spaulding | 6,475,226 B1 | 11/2002 | Belef et al. |
| 6,048,349 | A | 4/2000 | Winston et al. | 6,482,217 B1 | 11/2002 | Pintor et al. |
| 6,050,949 | A | 4/2000 | White et al. | 6,497,711 B1 | 12/2002 | Plaia et al. |
| 6,063,093 | A | 5/2000 | Winston et al. | 6,501,551 B1 | 12/2002 | Tearney et al. |
| 6,066,153 | A | 5/2000 | Lev | 6,520,975 B2 | 2/2003 | Branco |
| 6,068,603 | A | 5/2000 | Suzuki | RE38,018 E | 3/2003 | Anctil et al. |
| 6,068,638 | A | 5/2000 | Makower | 6,532,380 B1 | 3/2003 | Close et al. |
| 6,081,738 | A | 6/2000 | Hinohara et al. | 6,533,749 B1 | 3/2003 | Mitusina et al. |
| RE36,764 | E | 7/2000 | Zacca et al. | 6,561,998 B1 | 5/2003 | Roth et al. |
| 6,095,990 | A | 8/2000 | Parodi | 6,565,588 B1 | 5/2003 | Clement et al. |
| 6,099,542 | A | 8/2000 | Cohn et al. | 6,569,177 B1 | 5/2003 | Dillard et al. |
| 6,106,515 | A | 8/2000 | Winston et al. | 6,592,526 B1 | 7/2003 | Lenker |
| 6,110,121 | A | 8/2000 | Lenker | 6,620,180 B1 | 9/2003 | Bays et al. |
| 6,120,515 | A | 9/2000 | Rogers et al. | 6,623,437 B2 | 9/2003 | Hinchliffe et al. |
| 6,120,516 | A | 9/2000 | Selmon et al. | 6,623,495 B2 | 9/2003 | Findlay, III et al. |
| 6,126,649 | A | 10/2000 | VanTassel et al. | 6,623,496 B2 | 9/2003 | Snow et al. |
| 6,129,734 | A | 10/2000 | Shturman et al. | 6,629,953 B1 | 10/2003 | Boyd |
| 6,134,003 | A | 10/2000 | Tearney et al. | 6,638,233 B2 | 10/2003 | Corvi et al. |
| 6,152,909 | A | 11/2000 | Bagaoisan et al. | RE38,335 E | 11/2003 | Aust et al. |
| 6,152,938 | A | 11/2000 | Curry | 6,652,505 B1 | 11/2003 | Tsugita |
| 6,156,046 | A | 12/2000 | Passafaro et al. | 6,652,548 B2 | 11/2003 | Evans et al. |
| 6,157,852 | A | 12/2000 | Selmon et al. | 6,656,195 B2 | 12/2003 | Peters et al. |

| Patent/Publication | Date | Inventor(s) |
|---|---|---|
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |

| | | | |
|---|---|---|---|
| EP | 1 767 159 A1 | 3/2007 |
| EP | 1 875 871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | WO 93/16642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | WO 2006/058223 A2 | 6/2006 |
| WO | WO 2006/066012 A2 | 6/2006 |

OTHER PUBLICATIONS

Translation of Aug. 15, 2007 mailed Japanese Patent Office Action, Application No. 1999-139033 (4 pages).
Abstract of JP2206452A (1 page), 1990.
Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).
Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).
Abstract of DE 44 44 166 A1 (1 page), 1996.
Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Huang et al., "Optical Coherence Tomography," Science, 254:1178-1181 (1991).
International Search Report and Written Opinion of PCT Application No. PCT/US04/12600, dated Jun. 13, 2008, 8 pages total.
International Search Report of PCT Application No. PCT/US04/12601, dated Jun. 30, 2005, 3 pages total.
Mar. 27, 2009 Communication from the European Patent Office regarding EP Application No. 01 991 343.3 (7 pages).
Apr. 6, 2010 European Supplementary Search Report in European Application No. 04760156.2 (3 pages).
Sep. 21, 2010 International Search Report and Written Opinion for corresponding PCT Application No. PCT/US2010/032558 (14 pages).

HIGH CAPACITY DEBULKING CATHETER WITH DISTAL DRIVEN CUTTING WHEEL

CROSS-REFERENCES TO RELATED APPLICATION

This application is a continuation of U.S. patent application Ser. No. 11/934,680, filed Nov. 2, 2007, now U.S. Pat. No. 8,052,704 B2, issued Nov. 8, 2011, the contents of which are hereby incorporated by reference herein.

BACKGROUND OF THE INVENTION

Restriction of blood circulation due to the atherosclerotic build up of plaque in arteries is the source of much morbidity and mortality. Plaque deposits in cardiac arteries can result in angina and myocardial infarction. Plaque deposits in peripheral arteries of the limbs can result in peripheral artery disease (PAD).

PAD affects about 20% of the population over 70, and in more severe forms (which afflict about 2 million people in the US) can lead to non-healing ulcers, infection, and eventually loss of limb due to amputation. Most people die within two years of such amputations.

Although many techniques, such as stenting and balloon angioplasty, have been developed to help restore circulation to plaque occluded cardiac arteries, these methods tend to be less effective for peripheral arteries. Stents, although well suited to low-mobility cardiac arteries, tend to either restenose or frequently break in peripheral limb arteries because these arteries are subjected to greater movement and mechanical stress. Balloon angioplasty, which stretches the artery walls while it compresses and redistributes plaque, tends to cause greater and typically less acceptable amount of artery wall damage when it is used with peripheral arteries. Additionally, since angioplasty simply redistributes plaque rather than actually removing plaque, in the higher mobility peripheral arteries, the redistributed plaque tends to relatively quickly distribute itself back into an unacceptable configuration again.

From the surgical perspective, one of the most ideal ways to treat arteries blocked by plaque is to remove the plaque from the inside of the artery using an atherectomy catheter. Such catheters, which come in a variety of different designs, can be introduced into the body at a convenient location and threaded inside the artery to the plaque occluded target region (which can usually be determined exactly using fluoroscopy and appropriate radio opaque contrast dyes). Once they are at the correct region, atherectomy catheters then surgically remove the occluding plaque.

Many different types of atherectomy catheter devices have been proposed, including catheters with rotating burrs (Boston Scientific Rotablator), lasers to photo-dissolve tissue (Spectrametics Laser Catheter), and cutter-balloon catheters (Guidant AtheroCath). All have certain drawbacks, however, such as difficulty in traversing through small and torturous arteries to get to the plaque occluded target zone or zones.

One of the biggest problems plaguing prior art atherectomy catheters is the problem of gracefully handing the shaved plaque remnants. Some designs, such as the Rotablator, make no attempt at all to handle the liberated plaque fragments, and instead let the fragments migrate through the circulation. This can cause many problems, because the liberated plaque remnants can be thrombogenic, and can end up causing downstream occlusions. Other catheter designs attempt to reduce this problem by capturing the plaque shavings and safely removing them from the body. Capturing the plaque shavings also makes the samples available for pathologic and medical diagnostic examination, and may give important information as to the root causes behind the plaque build-up in the first place.

More recent atherectomy catheters, such as the Fox Hollow SilverHawk articulated rotating blade atherectomy catheter, have been designed to address such issues. The SilverHawk catheter (exemplified by U.S. patent application Ser. Nos. 10/027,418; 10/288,559; 10/896,747; and others) uses a unique rotating blade, window, and hinged hollow nose design, which can be controlled to either assume a straight position or an angled (drooped) position.

To use the SilverHawk atherectomy catheter, the operator will usually first insert a guide wire to the proper location, attach the SilverHawk to the guidewire, and introduce the SilverHawk through a convenient artery port, often located near the groin region. The operator maneuvers the SilverHawk device to the appropriate region of plaque, keeping the SilverHawk moveable angle nose in a straight configuration. Once at the target zone, the operator then bends or adjusts the angle of the SilverHawk's hollow nose. The nose contacts the artery wall opposite the plaque target, exerting pressure. Through the laws of physics, this generates an opposing pressure that in turn presses or "urges" the catheter's window and cutter against the target plaque region.

The operator will then spin-up the cutter, and move the catheter across the target zone. The rotary cutter cuts a thin strip of plaque, which is directed, by the motion of the cutter and the device's geometry, into the devices' hollow nose cone. The cuttings stay in the nose cone, where they can eventually be removed from the body and analyzed.

The SilverHawk atherectomy catheter represented a significant advance in the state of the art, because it enabled substantially longer regions (often several centimeters or more) of plaque to be shaved for each pass of the catheter over a region. An additional advantage was that the catheter could be rotated; exposing the window and the rotating blade to another region, and a target region of plaque could thus be shaved multiple times, allowing precise control over the amount and geometry of the plaque reduction process.

Although the SilverHawk catheter demonstrated the utility of this type of approach, further improvements were still desirable. In particular, the available plaque storage space in the device's hollow nose cone was limited, and improvements in trimming partially attached plaque shavings were also desirable.

The one problem with such prior art designs was that whenever the nose cone filled with plaque, the catheter needed to be pulled from the body, cleaned, and then laboriously rethreaded back to the correct location in the target zone again. This tended to significantly prolong the length and effort required for many medical procedures, and thus was undesirable to both physician and patient alike. Methods to reduce this burden were thus highly desirable.

Atherectomy design engineers face some formidable design challenges, however. In order to navigate the narrow and torturous arteries, veins and other lumens of the body, such catheters must have extremely small diameters, usually on the order of 1 to 3 millimeters (3-9 French). At the same time, the devices must be flexible enough to be threaded through such arteries, yet have sections that are rigid enough to accomplish the required positioning, cutting, and plaque storage functions.

Due to these many design constraints, mechanical designs that might be relatively simple to execute with larger diameter devices become very problematic at such extremely small diameters. Additional constraints, such as the need to use biocompatible materials, the need for extremely high reliability, and the need for accommodate a wide variety of different plaque targets in different patients make the design of such devices quite challenging.

BRIEF SUMMARY OF THE INVENTION

The present invention is an improved atherectomy catheter designed to overcome some of the limited plaque carrying capacity associated with prior art catheter designs. The present invention accomplishes this goal by departing from the conventional proximally driven rotary cutter designs employed by prior art atherectomy catheters, and instead teaches a novel, distally driven (or circumference driven) rotary cutter design.

Such distally (or circumference) driven designs are very non-intuitive, which is one of the reasons why prior art ignored or taught against such designs. Distally driven rotating cutter catheters require a break in the power transmission drive that links a proximal motor (usually located in a catheter handle outside of the body) with a circular cutter (located in the distal head of the catheter). Thus distally driven designs tend to require either a complex bypass-gear arrangement to communicate power to the rotary cutter from a direction away from the natural proximal direction of the drive motor, or alternatively require an entirely different rotary (torque) source, such as a miniaturized motors located in a distal location in the device's nose cone.

The present art teaches that such non-intuitive distal or circumference driven designs, although more complex, can have the unexpected advantage of now allowing plaque shavings to be stored in the larger volume hollow catheter body, rather than the limited catheter nose space. In some embodiments, even hollow tube of the catheter may be used for still more additional storage space.

This new design substantially increases the ability of the catheter to hold plaque shavings. This in turn translates into a direct benefit to both physicians and patients. The improved catheter can be operated for an appreciably longer period of time (i.e. clear substantially more plaque) before the operator needs to withdraw the catheter from the body for cleaning. This makes plaque procedures quicker, cheaper, more effective, (because more plaque can now be removed without undue hardship) and less stressful to patients and physicians. It also encourages more complete and careful plaque removal. A second advantage is that distal driven designs can also give the catheter an improved ability to trim dangling portions of plaque residue that are still hanging to artery walls.

In an alternative embodiment of the present invention, sensors may also be added to the design to help the operator properly position the device and also properly orient the cutting window of the device.

DETAILED DESCRIPTION OF THE INVENTION

The present art is normally intended for use with human patients, as well as various veterinary applications. For simplicity, this combined human or animal use will be referred to as use in mammals, although of course such devices could also be used in appropriate non-mammal animals such as birds, reptiles, and amphibians, etc., as appropriate.

It should also be understood that although the examples of cutting unwanted plaque deposits in arteries are used throughout this disclosure, the actual invention may be used for a broader variety of applications, including removing tumors, getting biopsies, etc. in arteries, veins, and any other tubular or roughly tubular body lumen.

For brevity, non proximally driven rotating cutter catheters will usually be referred to in the specification as distal driven designs. However it should be understood that wherever appropriate, alternative non-proximally driven designs such as circumference driven designs are also included in this general description.

Nomenclature: The handle end of the catheter is the proximal location, and the nose cone tip of the catheter is the distal location.

Figure 1:
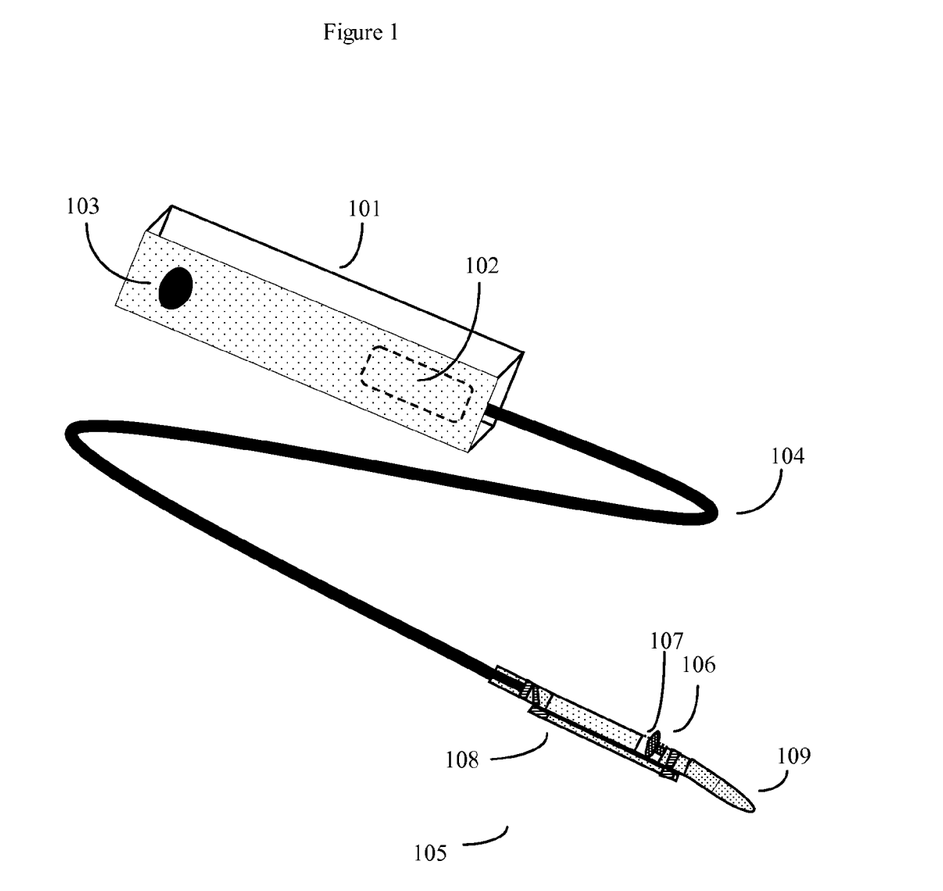
FIG. 1 shows an overview of the device

FIG. 1 shows an overview of the device. The device typically consists of an operator handle (101) which remains outside the body. The handle may optionally contain a battery, and a motor (102) which may provides torque for a rotary cutter, and additionally one or more optional control switches (103). The catheter also has a long narrow tube (shaft) (104), and the cutting atherectomy head (105). The catheter tube or shaft (104) will typically consist of a flexible tube, which is often hollow and capable of passing a guide wire, as well as optionally other materials such as drugs and contrast materials, control wires, drive shafts, sensors, sensor fibers or wires, ultrasonic signals, and the like.

In some embodiments, the hollow tube may contain a shaft or hollow shaft capable of transmitting torque from a motor mounted in the handle (102) to a rotary cutter (106) mounted in the atherectomy head. This rotary cutter (106) will usually be exposed to the outside environment through a window (107). The relative positions of the rotary cutter (106) and the window (107) may optionally be controlled by the operator, and optionally the cutter may be moved relative to the window edge to open or close the window (exposing or hiding the circular cutter) under operator control.

Torque may be communicated to the rotary cutter (106) by a variety of means so long as these means to not obscure either the window or the hollow space in the tube on the side of the catheter proximal to the window. Some of these torque (rotary motion) imparting means include indirect, off-axis, mechanical gearing or other means (108). In other embodiments, the catheter tube (104) may transmit electrical power, pressure, or chemicals capable of driving an electric motor, turbine, or chemical motor which can be mounted in the atherectomy head.

The head will also usually contain a flexible or moveable nose cone region or nose region (109), which in some embodiments may be connected to the rigid body of the head by one or more hinge pins or other means. This flexible nose-cone region will be capable of being deformed by the operator from a straight to a bent position so that the nose, by pressing against one wall of a body lumen, will generate an opposite force that will tend to move the cutter (106) and window (107) against an opposite wall of a body lumen, thus enabling the cutter to cut material from selected zones of a body lumen under operator control.

The catheter's nose (109) usually has a tapered or conical atraumatic design intended to allow the catheter head to easily migrate through arteries. It may be composed of softer materials, and may additionally have an internal coiled spring or other means to allow the tip to bend somewhat as needed to migrate through torturous arteries and other body lumen structures.

Figure 2A:
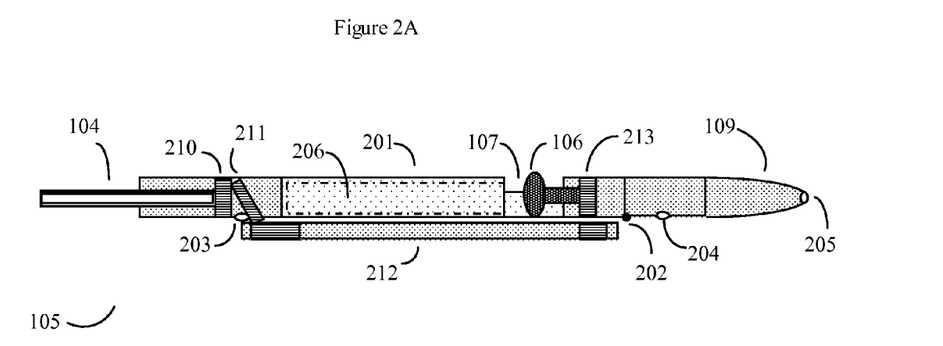
FIG. 2A shows a detail of the device's indirect distal driven rotating blade configuration

FIG. 2A shows a close-up of the cutting atherectomy head (105). The head will typically consist of a hollow body (201) connected to the catheter tube (104), and a tapered nose, (109) usually connected to the front (distal portion) of the hollow body by at least one hinge (202). The head (105) will additionally consist of at least a window (107) and rotating cutting wheel (106). The unit may also optionally have holes or ports (203), (204), (205) and appropriate inner hollow spaces for accommodating an optional guide wire. This optional guide wire helps the operator thread the catheter head through torturous arteries or other body lumens, and will be discussed in more detail in FIG. 4.

As previously discussed, prior art atherectomy catheter designs taught proximally driven rotating cutting wheel designs. That is, the rotating wheel would (106) would under previous art have been directly coupled to a drive shaft coming from catheter tube (104) by a coupling mechanism aligned with the axis of wheel (106).

The prior art proximal-drive teaching had certain advantages. It was compatible with simple and robust designs, and also minimized the cross-section (width) of the catheter head, which was again desirable because this helped the head migrate through torturous artery channels. The prior art proximal drive design also allowed large amounts of torque to be communicated through the drive shaft to the cutting wheel by rotation, and also allowed the relative angle of the cutting wheel to be adjusted in the catheter head by transverse motion of the rotating shaft relative to the outer catheter sheath. Thus an operator could, by transverse motion of the catheter's inner rotating shaft, both communicate rotation to the cutting head, and also adjust the cutting head's relative orientation to catheter head windows (opening and closing the window, for example) or alternatively, in fixed window designs, adjust the angle of the cutting head or control to what extent the cutting head protrudes out through a catheter window.

However, as previously discussed, the prior art proximal design had one big drawback. The drawback was that proximal drive rotary shaft and coupling mechanism occupied essentially all of the hollow space (206) in the inside of the catheter head (i.e. proximal to the window (107) and cutter (106). As a result, in prior art designs, the only space that was available to store cutter shavings (typically plaque shavings) was in the hollow nosecone (109). Unfortunately this hollow nosecone, which needed to be tapered in order to pass easily through arteries, typically had very limited internal volume and storage capacity.

Examples of such proximally driven cutters that store plaque shavings in the distal side in a conical nose include the previously discussed SilverHawk device. As previously discussed, this prior art device, although very functional, filled up quickly with shavings. When this happened, the device had to be stopped, removed from the body, the contents of the nose removed, and then reinserted into the body and threaded to the correct region again. As previously discussed, this was undesirable because it extended the length of procedures, and was burdensome for the physician and patient.

As previously discussed, by departing from the mechanically simpler proximally driven designs of prior art, and instead moving to a mechanically more complex non-proximally driven design (such as a distally driven or circumference driven design), the substantially larger space (206) on the proximal side of the cutter wheel (106) can now be opened up and used to store plaque shavings. Although due to the higher complexity, previous designs taught away from such configurations, this more complex design is justified by the subsequent savings in catheter cleaning time and effort. Whereas earlier designs, due to limited nosecone plaque storage space (109), could potentially waste hours of physician and patient times through tedious multiple removal and cleaning steps, these wasted hours can now be reduced or eliminated. The additional time can be used to do a more complete job of plaque removal as needed.

Given the extremely small diameter available to catheters, however, this alternative design poses many challenges. Either the rotating cutting wheel needs to be coupled to its rotational power source by an indirect linkage, or alternatively the cutting wheel needs to be powered from the distal end.

Various types of indirect linkage are possible, and the present invention is not intended to be limited to any one means. In one embodiment of the invention, the mechanism may involve indirectly coupling the cutting wheel (106) to the torque or rotation transmitting catheter drive shaft from the catheter tube (104) by an indirect gearing means so that torque is transmitted from the drive shaft to the outer diameter of the cutting wheel from the distal direction.

Figure 5A:
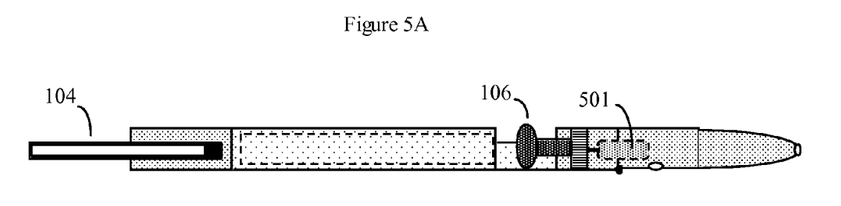
FIG. 5A shows an alternative device embodiment employing a distal electric motor or turbine to drive the cutting wheel.
Figure 5B:
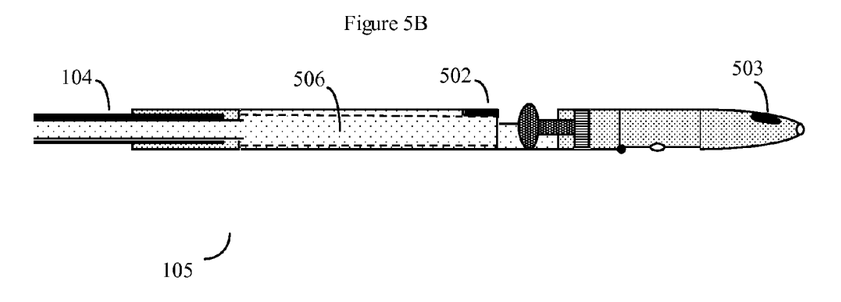
FIG. 5B shows an alternative device embodiment employing sensors to monitor the status of the artery and plaque near the device's cutting wheel.

In one example, a rotating drive shaft from the flexible catheter tube (104) turns a first axial aligned gear (210) which, through one or more transfer gears (211), transfers power to an off-axial drive shaft (212). This off-axial drive shaft (212), typically will be connected closely to the main body of the catheter head (201) by a coupling mechanism (not shown) that allows the drive shaft to rotate. Off-axial drive shaft (212) then transfers power to the rotating cutter (106) by a second gearing mechanism (213). Many other mechanisms are also possible, and these are discussed in more detail in FIG. 5.

A second advantage of the present invention's distal side driven design over the earlier proximal driven art is that the distal driven design allows the cutter wheel (106) to be mounted on a carriage mechanism (not shown) so that it can also be used to open and close the window (107) as directed by the operator. This can allow the cutter wheel to be gradually closed by the operator, so as to allow simultaneously shearing off and trapping any dangling plaque that still may be attached to the side of an artery wall.

As per the earlier SilverHawk catheter designs, usually, the angle of the present art catheter's nose (109), relative to the rest of the catheter head body (201), will be under the control of the operator so as to act to press the cutting wheel against the target plaque with the desired degree of pressure.

As per the earlier SilverHawk catheter design, plaque cutting can be facilitated by deflecting the cutting wheel (106) so that it protrudes slightly through the window (107). This way the exposed tip of the cutting wheel may freely shave away stiff regions of exposed plaque that might not otherwise bend to extend inside the catheter window. This deflection may be achieved by a cam mechanism (not shown). Cam mechanisms of this type were previously taught by application Ser. Nos. 10/896,741; 10/288,559; 10/027,418, the contents of which are incorporated herein by reference.

The rotating cutting wheel may have sharp edges composed of tungsten carbide and the like. In other configurations, a wheel need not be used, and instead an alternate cutting device such as laser, radio frequency electrodes, ultrasonic vibrating knifes, may be used. In still other configurations, a cutting wheel can have its cutting effectiveness enhanced by coupling its rotary cutting action with laser, radio frequency electrodes, ultrasonic vibration, and the like as needed.

Device dimensions: Typically the catheter cutting head (201) will have a diameter between about 1 to 2.2 millimeters. The cutting window (107) will typically have a length of about 1.2 to 2.5 millimeters. In embodiments where the cutting wheel contains a cam or other orientation control mechanism that allows the wheel to extend slightly outside the window, the wheel orientation control mechanism may allow the wheel to at least temporarily be locked into a position that allows the cutting outer edge of the wheel to extend about 0.025 to 0.64 mm outside the cutting window. This allows the operator to move the catheter head along the target region of plaque, and shave off a long thin portion of this plaque while doing so.

The cutting wheel (106) will typically have a diameter of about 1.14 mm, and may have a straight edge, a beveled edge (which allows removal of plaque without damaging the underlying artery lumen), or a fluted edge depending upon the needs of the specific application. Usually the cutting wheel will be mounted on a shuttle or cam mechanism to allow the operator to adjust the protrusion of the wheel from the window, or alternatively the angle of the wheel or even the location of the wheel relative to the window opening (causing the window to be open, partially closed, or fully closed by the wheel).

The cutting wheel will typically rotate at speeds appreciably faster than 100 rotations per minute (rpm), preferably about 8,000 rotations per minute (rpm).

The cutting edge of the blades may be optionally hardened by an appropriate coating, such as ME-92, tungsten carbide, or other suitable materials as taught by U.S. Pat. Nos. 4,771,774; 5,242,460; 5,312,425; 5,431,673; and 5,674,232, the contents of which are in herein by reference.

As previously discussed, the action of blade can be facilitated by ultrasonic vibration, laser cutting, radiofrequency electrodes, and the like. If this option is elected, appropriate mechanisms (i.e. a piezoelectric ultrasonic vibrator, laser diode or optical fiber, electrodes, etc.) may also be provided in the catheter head to drive the blade as needed. If the action of the ultrasonic, laser, or electrode cutter is sufficiently robust enough as to make it a spinning blade unnecessary, then the blade may either not be spun up, or the blade rotary mechanism may be omitted, or a non-rotating blade may be used.

In many embodiments, it will be useful to allow the location and orientation of the catheter head (201), nose (109), and cutting window/wheel region (106/107) to be identified by x-ray fluoroscopy by constructing these regions out of suitable combinations of translucent and radio opaque materials, thus, for example, enabling the region distal to the cutting head to be distinguished from the region proximal to the cutting head.

In addition to fluoroscopy localization, other modalities, such as light (optical) and sonic (ultrasonic) localization methods may also be used. Here orientation may be facilitated by running a fiber optic strand through the catheter (104) (not shown) to an appropriate location on the catheter head, and determining the location and orientation of the head by optical means. Alternatively an ultrasonic transducer or pickup may be incorporated into the catheter head.

Typically the flexible outer catheter tube (104) between the handle (101) and the head (105) will have a length between 50 cm and 200 cm, a diameter between 1 French (0.33 mm) and 12 French (4 mm), and will usually be between 3 French (1 mm) and 9 French (3 mm) in diameter. The catheter body will often be made from extruded organic polymers such as polyvinylchloride, polyurethane, polyester, polytetrafluoroethylene (PTFE), silicon rubber, or similar materials. The catheter body may be reinforced as needed with wires, coils, or filaments as needed to give the body additional strength and to control rigidity and pushability.

Portions of the catheter head (105) (distal region of the catheter) will often be rigid or partially rigid, and can be made from materials such as metals, hard plastics, composite materials, NiTi steel (optionally coated with titanium nitride, tantalum, ME-92® or diamonds. Usually stainless steel or platinum/iridium will be used. The length of the middle portion of the catheter head may often vary between about 5 to 35 mm (201), and will usually be between about 10 to 25 mm, however alternative lengths (longer or shorter) may also be used.

As previously discussed, the extreme distal end of the catheter head (the nose) (109) will usually be made to be both flexible and atraumatic so as to allow the catheter to be threaded through arteries, veins, or other body lumens with maximum ease and minimum trauma. Because, in this design, the nose is no longer used to store plaque, this nose design may be optimized to accommodate the distal drive mechanism and also optimized to allow easy passage of the catheter through arteries. In some cases, the distal tip will have an inner coil construction to maximize flexibility. The distance between the rigid part of the catheter head and the distal end tip of the flexible catheter nose will typically be between 10 and 30 mm, but may vary as needs dictate.

Figure 2B:
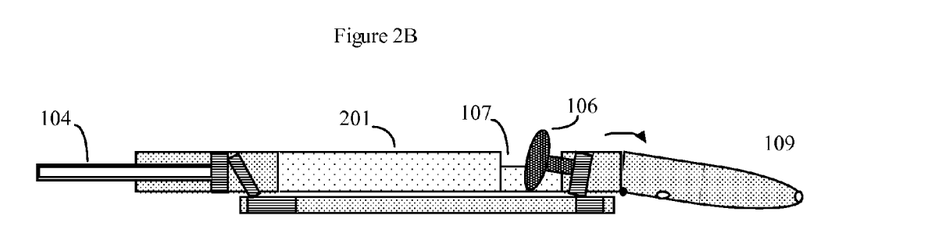
FIG. 2B shows a detail of the device's swiveling nose cone design.

FIG. 2B shows the catheter head with the catheter nose cone (109) in the angled, drooped or bent configuration. Typically this nose angle will be adjustable by the operator, either through a cam mechanism (not shown) coupled through the catheter tube (104) to the operator handle (101), or through selection of materials with appropriate rigidity/elasticity and bendability so that the operator may adjust the nose angle to an appropriate level by pulling or pushing on the catheter handle (101) and tube (104).

FIG. 2B shows that in this configuration, nose cone (109) is bent relative to body (201). This bending is a simple way to effectively increase the cross sectional area of the catheter, and is used to force the cutting edge of the catheter against the appropriate target zone. In the confines of a narrow body lumen such as an artery, nose cone (109) is deflected until it contacts a body lumen wall (i.e. the opposite wall of the artery). This pushes (or "urges") cutting window (107) and cutter (106) in the opposite direction. If appropriately directed, this will push, force, or urge the cutter against the appropriate target zone (usually a region of the artery occluded or partially occluded with plaque). Once the cutter is in proper position, with the correct amount of "force" or "push" dialed in by the angle of the nose deflection, the catheter can then be moved by the operator, shaving away unwanted plaque material.

Figure 3:
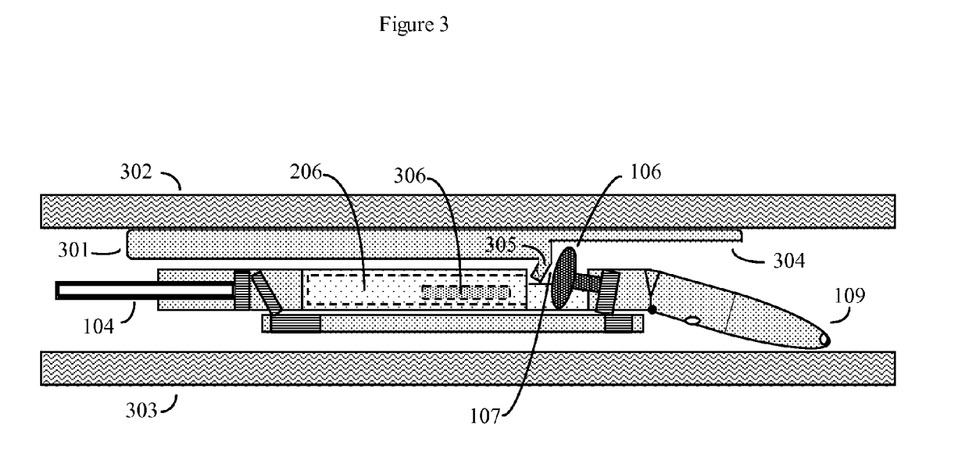
FIG. 3 shows how the device cuts plaque in an artery.

FIG. 3 shows a diagram of the catheter head of the present invention cutting plaque (301) from an artery wall (302). In this configuration, the catheter's nose (109) has been deflected at enough of an angle to contact the opposite artery wall (303). The cutting wheel (106) has been forced up against the plaque (301) and has already cut away a section of this plaque (304). A dangling region of plaque (305) is entering the hollow catheter body (206) through the window (107). Here, the operator controls the speed and extent of plaque removal by using control (101) to partially retract the catheter head over the plaque by pulling on catheter tube (104), while wheel (106) is spinning and exposed to the plaque through window (107). Excess plaque (306) is stored in the hollow region of the catheter head (206). The drawing is not to scale, in actuality; the available storage space (206) will typically be substantially larger than the storage space of nosecone (109).

Often, it may be advantageous to use a guidewire as a type of monorail to quickly direct catheters to the correct target zones. Usually such guidewires will have diameters between about 0.010" and 0.032", usually around 0.014. When this option is desired, the catheter may be designed to be compatible with guidewire use.

Figure 4:
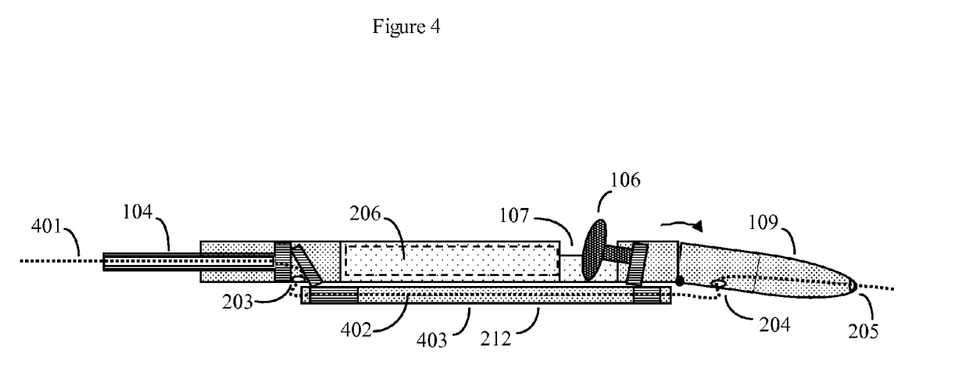
FIG. 4 shows how the device can interact with a guide wire.

FIG. 4 shows one possible way in which the catheter of the present invention may work with a guide wire. In this example, guidewire (401) is threaded up through hollow catheter tube (104). In order to allow the head's cutting mechanism to operate freely and without risk of entanglement from a guide wire, it may be useful to have the guide wire exit from the main catheter tube through a first proximal exit port on the head (203), thus skipping the storage area (206) window (107) and plaque cutting (106) regions of the head. In this configuration, the guide wire would then typically reenter the nose cone (109) at opening (204), travel through the nose end of the head for a short distance, and then finally exit the head again through a third exit port or opening (205), often located near the tip of the catheter's nose (109) at the extreme distal end of the catheter In some embodiments, it may also be desirable to protect the portion or portions of the guidewire that is briefly external to the catheter head (402) by a guidewire tube/lumen or a telescoping guidewire tube/lumen (403). Such guidewire protection lumens may have a length between about 2 and 14 cm, or even longer as needed to accommodate longer heads with higher plaque storage volumes. This telescoping guidewire lumen protects both the guidewire and the patient's artery linings from inadvertent excessive pressure while the catheter head traverses narrow arteries, and also insures that the guidewire never comes into contact with window (107) or cutter (106).

In some embodiments, the telescoping guidewire lumen may serve a secondary purpose by also acting as a means to transmit torque (212) from a rotating shaft in the catheter tube (104) to the cutting wheel (106) as previously shown and discussed in FIG. 2A. This dual-action role (guidewire protection/torque transmission) helps to minimize the cross section area of the catheter head when an off-axis drive mechanism is used.

In still another embodiment, lumen (403)/drive shaft (212) can consist of one or more nested hollow tubes so that an inner tube may rotate and conduct torque to drive wheel (106), yet the outer part of the lumen may be substantially stationary as to avoid tangling with a body lumen. The guide wire may still progress through the hollow inner core of this nested structure.

Many other combinations of drive mechanisms, catheter configurations, and sensor configurations are also possible, and some of these are shown in FIGS. 5A and 5B.

As shown in FIG. 5A, the rotary cutter (106) does not necessarily have to be coupled to a rotating shaft of any sort from catheter tube (104). Rather, the rotary cutter may be adequately driven from the distal end of the catheter by means of a small electric motor or turbine (501). This motor or turbine may in turn derive power from catheter tube (104) and in some embodiments handle (101) as well by appropriate wires or miniature pressure or chemical tubes (not shown) progressing up catheter tube (104).

As shown in FIG. 5B, in some embodiments, the catheter head (105) may additionally have various imaging or positional sensors, such as ultrasound transducer arrays, optical fibers, coherence tomography devices, infrared sensors, directional ultrasonic sensors, etc. mounted on the catheter head or nose region (502), (503). In one embodiment, the orientation of the sensor or sensors may be directed by the operator to give information as to the status of the plaque and/or artery of or other body lumen that is facing the cutting window of the catheter. This can allow the operator to determine if the catheter is in the proper orientation relative to its intended target. Examples of such sensors were described in more detail in application Ser. No. 10/421,980, the contents of which are incorporated herein by reference.

FIG. 5B also shows yet another embodiment in which the plaque storage container (506) is extended to now also include some of the hollow core of the catheter tube itself (104). With this configuration, handle (101) may be hooked up to a suction or cleaning device, as needed, to give the catheter a near infinite ability to accommodate plaque shavings. With this configuration, the catheter need never be removed from the body until the complete plaque removal task is accomplished.

What is claimed is:

1. A catheter for removing tissue comprising:
   an elongate body having a proximal end and a distal end and a tubular side wall having an outer surface defining an outer dimension of the elongate body and an inner surface defining a lumen, the elongate body having a distal portion with a window in the side wall, the lumen proximally adjacent the window comprising a material collection chamber;
   a rotational tissue cutting element disposed at least partially within the lumen of the elongate body, the tissue cutting element having a distal side and a proximal side, the tissue cutting element having an axis of rotation that extends through the material collection chamber;
   a source of rotational power; and
   a drive shaft connected between the source of rotational power and the distal side of the rotational tissue cutting element, no portion of the drive shaft being contained within the material collection chamber, such that the material collection chamber is substantially open for collection of tissue.

2. The catheter of claim 1, wherein the source of rotational power is positioned within the elongate body at a location distal to the tissue cutting element.

3. The catheter of claim 1, further comprising a handle connected at the proximal end of the elongate body, the source of rotational power being contained within the handle.

4. The catheter of claim 1, in which the source of rotational power is one of a mechanical coupling to a rotating shaft, an electric motor, a pressure powered turbine, or a chemical powered turbine.

5. The catheter of claim 2, wherein the drive shaft includes a proximal portion having an axis of rotation that generally coincides with the axis of rotation of the tissue cutting element and a distal portion having an axis of rotation that is radially off-set from the axis of rotation of the tissue cutting element and from the axis of rotation of the proximal portion.

6. The catheter of claim 5, further comprising a first gear element connected to transfer torque from the proximal portion of the drive shaft to the distal portion of the drive shaft.

7. The catheter of claim 6, further comprising a second gear element connected to transfer torque from the distal portion of the drive shaft to the distal side of the tissue cutting element.

8. The catheter of claim 1, wherein the drive shaft has first and second ends positioned within the elongate body distal of the rotational tissue cutting element.

9. The catheter of claim 1, wherein the elongate body further comprises a deflectable nose region, and a mechanism to allow an operator to deflect the nose region against a body lumen, thereby pushing the window and the rotatable tissue cutting element against an opposite wall of the body lumen, allowing the rotatable cutter to cut material from said body lumen.

10. The catheter of claim 1, wherein the elongate body contains openings for receiving a guidewire.

11. The catheter of claim 1, wherein the distal portion of the elongate body further comprises an RF electrode, a laser, or an ultrasound emitter.

12. The catheter of claim 1, wherein the distal portion of the elongate body further comprises an imaging device.

13. The catheter of claim 12, in which the imaging device is selected from the group consisting of ultrasound transducer arrays, optical fibers, and coherence tomography devices.

14. The catheter of claim 1, further comprising a source of ultrasonic vibration operatively coupled to the rotatable tissue cutting element, the source of ultrasonic vibration being configured to ultrasonically vibrate the rotatable tissue cutting element.

15. The catheter of claim 14, wherein the source of ultrasonic vibration is a piezoelectric ultrasonic vibrator.

\* \* \* \* \*